United States Patent [19]
Treacy et al.

[11] Patent Number: 5,246,936
[45] Date of Patent: Sep. 21, 1993

[54] METHODS AND COMPOSITIONS CONTAINING PESTICIDES AND STILBENE COMPOUNDS FOR ENHANCED PESTICIDAL ACTIVITY

[75] Inventors: Michael F. Treacy, Newtown; Bruce C. Black; Stephen F. Donovan, both of Yardley, all of Pa.

[73] Assignee: American Cyanamid Company, Stamford, Conn.

[21] Appl. No.: 812,513

[22] Filed: Dec. 20, 1991

[51] Int. Cl.$^5$ ............... A01N 43/50; A01N 43/52; A01N 43/54; A01N 43/62
[52] U.S. Cl. ................... 514/256; 514/183; 514/218; 514/395; 514/401; 514/576
[58] Field of Search .......... 514/256, 576, 183, 218, 514/395, 401

[56] References Cited

U.S. PATENT DOCUMENTS

| | | | |
|---|---|---|---|
| 3,878,201 | 4/1975 | tomcufcik | 260/240 |
| 4,087,525 | 5/1978 | Lovell | 424/244 |
| 4,659,857 | 4/1987 | Kuhn | 588/58 |
| 4,775,693 | 10/1988 | Kihn | 514/522 |
| 5,124,149 | 6/1992 | Shapiro et al. | 424/93 T |

OTHER PUBLICATIONS

Holt et al., Fluorescent Whitening Agents. II.* Covalent Binding to Proteins during Irradiation by Sunlight, Aust. J. Biol. Sci., vol. 27, pp. 23–29 (1974).

Milligan et al., Fluorescent Whitening Agents. I. Bis-4,-4'-(methoxy-phenoxy-s-triazinylamino) stilbene-2,-2'-disulphonic Acid: Its Photodecomposition in Solution and on Wool, Aust. J. Chem., vol. 27, pp. 195–203 (1974).

Haigler et al., Calcfluor White ST Alters the in vivo Assembly of Cellulose Microfibrils, Science, vol. 210, pp. 903–905 (Nov. 21, 1980).

R. P. Jaques, The inactivation of the nuclear polyhedrosis virus of Trichoplusia ni by gamma and ultraviolet radiation, Canadian J. Microbiology, vol. 14, pp. 1161p14 1163 (1968).

Shapiro et al., Ultraviolet Protectants of the Gypsy Moth (Lepidoptera: Lymantriidae) Nucleopolyhedrosis Virus, Environ. Entomol., vol. 12, pp. 982–985 (1983).

Martignoni et al., Lab. Eval. of New UV Absorbers for Protection of Douglas-fir Tussock Moth Baculovirus, J. Econ. Entomol., vol. 78, pp. 982–987 (1985).

R. F. Chapman, The Insects: Structure and Function, 2nd ed., p. 46 (American Elsevier Publishing Co., Inc. 1971).

Hollinghaus et al., Toxicity, Penetration, and Metabolism of AMDRO in the Tobacco Budworm by Various Methods of Appl. Pesticide Biochem. & Physiol., vol. 22, pp. 329–336 (1984).

Chemical Patents Index, Documentation Abstracts Journal, Sec. Ch, Week 9123, 7 Aug. 1991, Derwent Publications Ltd., London, GB & US Published patent application, Ser. No. 07/609,848 (US Agric Res Serv) Apr. 23, 1991.

Martignoni et al., "Laboratory Evaluation of New Ultraviolet Absorbers for Protection of Douglas-Fir Tussock Moth (Lepidoptera–Lymantriidae) Baculovirus," J. Eco. Entomol. 78(4):982–987 (1985).

*Primary Examiner*—Allen J. Robinson
*Attorney, Agent, or Firm*—Alice C. Brennan

[57] ABSTRACT

The present invention describes a composition for enhanced pesticidal activity comprising a pesticide or a mixture of pesticides and a potentiating amount of a stilbene compound. This invention further describes a method for enhancing pesticide toxicity against an insect, an acarina, a mollusk or a nematode which employs the sequential or concurrent application of a pesticide and a stilbene compound.

5 Claims, No Drawings

METHODS AND COMPOSITIONS CONTAINING PESTICIDES AND STILBENE COMPOUNDS FOR ENHANCED PESTICIDAL ACTIVITY

BACKGROUND OF THE INVENTION

1. Field of the Invention

The present invention relates to the novel use of stilbene compounds to effectively enhance the toxicity of one or more chemical pesticides. The invention further relates to new compositions containing stilbene compounds and the chemical pesticide(s).

2. Description of the Related Art

Although several commercial formulations of entomopathogens (e.g., viruses and bacteria) have been available for many years, their use in agricultural and forestry pest management programs has been rather limited when compared to use of conventional insecticides. In general, efficacy of currently available formulations of entomopathogens has been considered to be inferior to that of conventional insecticides. Two factors commonly associated with inadequate efficacy of entomopathogens against pestiferous insects are (1) length of time required to subdue the pest (i.e., unacceptable level of crop-damage may occur before the pest succumbs to factors associated with pathogenic infection) and (2) short residual effectiveness against pest infestation (e.g., stability of entomopathogenic viruses is adversely affected by exposure to ultraviolet solar radiation; Jaques, Can. J. Microbiol., 14: 1161-1163 (1968)).

Doan et al. (J. Insect Pathol., 6: 423-429 (1984)) suggested that greater insect control could occur with the use of viruses if the formulation could be enhanced by the addition of certain adjuvants. Potential virus adjuvants included selected analogs or salts of the stilbene compound, 4,4'-diamino-2,2'-stilbene disulfonic acid. Two such analogs are Calcofluor White and Phorwite (Shapiro et al., U.S. Pat. NO. 5,124,149. Results from several laboratory studies reported by Shapiro et al. demonstrated that Calcofluor White M2R potentiated (as much as 1000-fold) the virulence of the nuclear-polyhedrosis virus (NPV) against the gypsy moth larvae, Lymantria dispar (as determined by enhanced $LT_{50}$ and $LD_{50}$ values). Shapiro et al., however, made no claims or suggestions regarding the use of stilbene compounds as enhancers of chemical pesticides (i.e., nonentomopathogens).

Although the mode-of-action pertaining to the stilbene's ability to potentiate the virulence of a virus against an insect is still speculative, there are reports in the literature regarding the biological properties of stilbene compounds. Stilbenes, and at least some of their photoproducts, have been shown to irreversibly bind to proteins in wool, silk, bovine serum albumin and apomyoglobin (Holt et al., Aust. J. Biol. Sci., 27: 23-29 and 195 (1974)). It has been demonstrated that certain stilbene compounds can inhibit cellulose and chitin microfibril formation (Roberts et al., J. Cell Biology, 9: 115a (1981); Herth, J. Cell Biology, 87: 442-450 (1980)). The stilbene, Calcofluor White, prevented formation of cellulose microfibrils in Acetobacter xylinum by hydrogen bonding with glucan chains (Haigler et al., Science, 210: 903-906 (1980)) and inhibited chitin synthetase activity in Neurospora crassa (Selitrennikoff, Exp. Mycol., 8: 269-272 (1984)). Shapiro et al. found that another stilbene compound, Phorwite AR, synergized a cytoplasmic polyhedrosis virus (CPV) against gypsy moth larvae. Since CPV multiplies only in the midgut epithelial cells, it has been suggested that the site of action of the brightener was the insect's midgut (Dougherty et al., "Mode of Action of Fluorescent Brighteners as Enhancers for the Lymantria dispar Nuclear-polyhedrosis Virus (Ld NPV) in the Gypsy Moth," oral presentation, Am. Society for Virology, Colorado State University, Fort Collins, Colo., Jul. 9, 1991). With the exception of some fluid-feeding species, many insects possess a midgut which is lined with peritrophic membrane, which in turn, is comprised of chitin and protein (Chapman, The Insects Structure and Function, p. 46 (Elsevier, N.Y. 1971)).

By way of additional background, U.S. Pat. No. 3,878,201 discloses certain pentadien-3-one substituted amidino hydrazones and the salts thereof. U.S. Pat. No. 4,087,525 describes the insecticidal use of these pentadienone hydrazone compounds. However, in practice, a representative hydrazone compound, hydramethylnon, has been shown to be a relatively poor contact insecticide and fair stomach insecticide against lepidopterous larvae (Hollingshaus et al., Pesticide Biochem. and Physiol., 22: 329-336 (1984)). In their 1984 study, Hollingshaus et al. found that when treated foliage was fed to larvae of tobacco budworm, Heliothis virescens, only around four to eight percent of the initial dose of hydramethylnon ever absorbed through the gut and into the hemolymph during the first 72 hours posttreatment. Most of the hydramethylnon was adsorbed to gut contents and tissue or excreted in the feces. If action sites for hydramethylnon exist outside of the insect's gut, the aforementioned data would suggest that hydramethylnon is a fairly inefficient toxin (since only 4% to 8% of the entire dose would ever reach those action sites). Other pesticides having similar activity like the pentadienone hydrazones include the insecticide rotenone as well as the insecticidal and acaricidal cinnamamide compounds. The cinnamamides are described in U.S. Pat. Nos. 4,659,857 and 4,775,693. As a consequence of the inefficiency of these pesticidal compounds in practical use, it is highly desirable to find a means for enhancing the absorption of the active ingredient through a lepidopteran's gut and thus improve or hasten movement of the toxin to action sites.

OBJECTS OF THE INVENTION

It is therefore an important object of the present invention to provide a method for the potentiation of chemical insecticides which have low absorptive or penetrative properties through an insect's gut upon ingestion.

Another object is to provide an improved method for combatting pests which involves jointly treating a crop, the habitat of the pests or other desired areas with a chemical pesticide and a stilbene compound.

A further object is to provide a highly unique pesticidal composition which possesses significantly enhanced pesticidal potency.

Further purposes and objects of the present invention will appear as the specification proceeds.

With the foregoing and other objects in view, the invention herein provides a composition comprising a chemical pesticide or a mixture of pesticides in combination with a stilbene compound. The products of this invention are highly efficacious against phytophagous insects. The background of the invention and its departure from the art will be further described hereinbelow.

SUMMARY OF THE INVENTION

The present invention describes a method for enhancing the toxicity of chemical pesticides against insects, acarina, mollusks or nematodes which employs the simultaneous or sequential application of a pesticide and a stilbene compound. This invention also involves a composition having enhanced pesticidal activity which comprises a pesticide or a mixture of pesticides and a stilbene compound.

DETAILED DESCRIPTION OF THE INVENTION

In accordance with the present invention, there is provided a novel method for enhancing the pesticidal activity of chemical pesticides which employs a pesticide or a mixture of pesticides and a stilbene compound wherein the stilbene compound beneficially potentiates the biological potency of the chemical pesticide(s).

The invention further relates to a method for enhancing pesticidal toxicity against insects, acarina, mollusks or nematodes by contacting the insects, acarina, mollusks or nematodes with, and/or applying to their habitat or food supply, an insecticidally, acaricidally, molluscicidally or nematocidally effective amount of an insecticide, an acaricide, a molluscicide or nematocide concurrently or sequentially with a potentiating amount of a stilbene compound. The invention also relates to an improved method for protecting agronomic crops, trees, shrubs, ornamentals and the like, from attack by pests, by applying to the plants a chemical pesticide in conjunction with the potentiating amount of the stilbene compound.

The pesticides which are particularly useful in the present invention embrace those toxic compounds which work as stomach and contact poisons, for example, the pentadienone hydrazones, rotenone, the cinnamamides and the like.

A preferred class of insecticides useful in the present invention are the pentadienone hydrazones having the following structure of formula I:

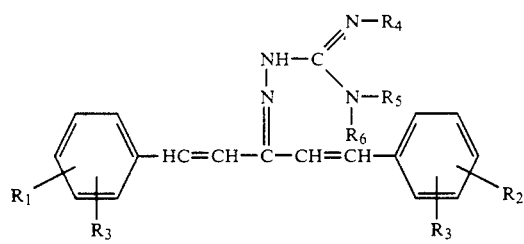

wherein $R_1$ and $R_2$ each represent hydrogen, halogen, $CF_3$, $C_1$-$C_4$ alkyl, $C_1$-$C_4$ alkoxy or $C_1$-$C_4$ alkylthio; $R_3$ is hydrogen or methyl, provided that when $R_3$ is methyl, $R_1$ and $R_2$ are also methyl; $R_4$ and $R_5$ represent hydrogen or $C_1$-$C_4$ alkyl, and When taken together, an alkylene group of 2 to 6 carbon atoms, a methyl substituted or a phenyl substituted alkylene group of 2 to 4 carbon atoms, a dimethyl substituted alkylene group of 2 to 4 carbon atoms or 1,2-cyclohexylene; and $R_6$ is hydrogen or $C_1$-$C_4$ alkyl; and salts thereof. The term "halogen" as used herein, is intended to mean chloro, fluoro, bromo and iodo, but chloro and bromo are favored. A particularly preferred pentadienone hydrazone is 1,5-bis($\alpha,\alpha,\alpha$-trifluoro-p-tolyl)-1,4-pentadien-3-one (1,4,5,6-tetrahydro-5,5-dimethyl-2-pyrimidinyl) hydrazone, known generically as hydramethylnon.

Of particular interest, the insecticidal and protecting agents for crops in combination with the stilbene potentiating agents have the above structure, wherein $R_1$ and $R_2$ are the same and the substituent is H, Cl, Br, $CF_3$, $C_1$-$C_3$ alkyl, methoxy or methylthio; $R_3$ is hydrogen; $R_4$ and $R_5$ each represent hydrogen, $C_1$-$C_3$ alkyl, $C_2$-$C_6$ alkylene or methyl, dimethyl or phenyl $C_2$-$C_4$ alkylene; $R_6$ is hydrogen; and the salts thereof, preferably the hydrochloride, hydrobromide or hydroiodide.

Preferred compounds are those described above, wherein $R_1$ and $R_2$ are each p-chloro or p-$CF_3$; $R_3$ and $R_6$ are hydrogen; and $R_4$ and $R_5$ are taken together and are $C_2$-$C_6$ alkylene or methyl, dimethyl or phenyl $C_2$-$C_4$ alkylene; and the salts thereof, notably the hydrochloride, hydrobromide or hydroiodide.

Still more preferred are compounds described above, wherein $R_1$ and $R_2$ are each p-chloro or p-$CF_3$; $R_3$ and $R_6$ are hydrogen; and $R_4$ and $R_5$ are taken together and are $C_2$-$C_6$ alkylene or methyl, dimethyl or phenyl $C_2$-$C_4$ alkylene; and the salts thereof.

Another class of insecticidal and acaricidal compounds which are useful in the practice of this invention are the cinnamamides having the following structure of formula II:

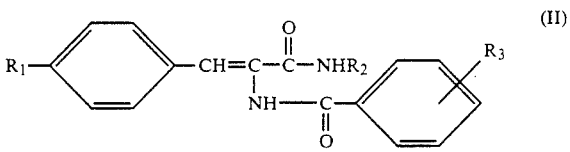

wherein $R_1$ is hydrogen, $C_1$-$C_4$ alkyl, $C_1$-$C_4$ alkoxy, $CF_3CH_2O$, $CF_3O$, F, Cl, Br, $CF_3$, $NO_2$, $CF_2HS$, $CF_2HO$, $(R)_2N$, $R$-$SO_3$, $R$—CO— NH or $CHY_2CF_2O$; Y is F, Cl or Br; R is $C_1$-$C_4$ alkyl; $R_2$ is $CH_3$, $C_2H_5$, branched $C_3$-$C_5$ alkyl or cyclopropyl; $R_3$ is hydrogen, Cl, $C_1$-$C_4$ alkyl, $C_1$-$C_4$ alkoxy or CN. Preferred cinnamamides include the structures wherein $R_1$ is $CF_3CH_2O$, $CF_3O$, F, Cl, Br, $CF_3$, $NO_2$, $CF_2HS$, $CF_2HO$, $R$—$SO_3$, $R$—CO—NH or $CHY_2CF_2O$; $R_3$ is hydrogen and Y, R and $R_2$ are as above described.

Representative compounds of formula II would include, but are not limited to, $\alpha$-benzamide-N-isopropyl-p-(1,1,2,2-tetrafluoroethoxy)cinnamamide, $\alpha$-benzamido-p-chloro-N-isopropylcinnamamide, $\alpha$-benzamido-p-fluoro-N-isopropylcinnamamide, $\alpha$-benzamido-p-hydroxy-N-isopropylcinnamamidemethanesulfonateester, $\alpha$-benzamido-N-cyclopropyl-p-(trifluoromethoxy)cinnamamide, $\alpha$-benzamido-N-isopropyl-p-(trifluoromethoxy)cinnamamide, $\alpha$-benzamido-p-(difluoromethoxy)-N-isopropylcinnamamide, $\alpha$-benzamido-N-cyclopropyl-p-fluorocinnamamide, $\alpha$-benzamido-N-cyclopropylcinnamamide, $\alpha$-benzamido-N-sec-butyl-p-(difluoromethoxy)cinnamamide and $\alpha$-benzamido-p-hydroxy-N-isopropylcinnamamide ethanesulfonate ester.

Examples of the potentiating agents useful in this invention include, but are not limited to, stilbenes such as triazinylstilbenes (e.g., bistriazinylaminostilbene and the like) or aroylstilbenes such as phenylureidostilbenes (Phorwite RN); etc. For instance, the stilbene compounds would encompass 4,4'-diamino-2,2'-stilbene disulfonic acid; 4,4'-diacetamidostilbene-2,2'-disulfate; 2,2'-(1,2-ethenediyl)bis-[5-(4-phenyl-2H-1,2,3-triazol-2-yl)]benzenesulfonic acid, dipotassium or disodium salt;

2,2'-(1,2-ethenediyl)bis[5-[4-(4-morpholinyl)-6-(phenylamino)-1,3,5-triazin-2-yl]amino]-benzenesulfonic acid,, disodium salt; 2,2'-(1,2-ethenediyl)bis[5-[[4-[(2-hydroxyethyl)methylamino]-6-(phenylamino)-1,3,5-triazin-2-yl]amino]benzenesulfonic acid, disodium salt; 2,2'-(1,2-ethenediyl)bis[5-[[4-[bis(2-hydroxyethyl)amino]-6-(phenylamino)1,3,5-triazin-2-yl]amino]-benzenesulfonic acid, disodium salt; 2,2'-(1,2-ethenediyl)bis[5-[4-methoxy-6-(phenylamino)-1,3,5-triazin-2-yl]amino]-benzenesulfonic acid, disodium salt; 2,2'-(1,2-ethenediyl)bis[5-[(phenylamino)carbonyl]amino]-benzenesulfonic acid, disodium salt; 2,2'-(1,2-ethenediyl)bis[5-[1,4-dihydro-4-oxo-6-(phenylamino)-1,3,5-triazin-2-yl]amino]-benzenesulfonic acid, disodium salt; 2,2-(1,2-ethenediyl)bis[5-[[4,6-bis(phenylamino)-1,3,5-triazin-2-yl]amino]-benzenesulfonic acid, disodium salt; etc. Analogs or photoproduct derivatives of the stilbene compounds are contemplated as embraced by this invention. Of course, the conventional salts of each stilbene compound, such as, sulfate, sulfonate, sodium, potassium, ammonium, etc., are also included in the invention.

Preferred potentiating agents are the analogs of 4,4'-diamino-2,2'-stilbene disulfonic acid, namely, a Calcofluor White (available from Sigma Chemical Co., St. Louis, Mo.) such as Calcofluor White M2R, Calcofluor White ABT, Calcofluor White LD, Calcofluor White RWP, etc.; a Blancophor (available from Mobay Chemicals, Pittsburg, Pa.) such as Blancophor BBH, Blancophor MBBH, Blancophor BHC, etc.; an INTRAWITE ® (a heterocyclic stilbene derivative, available from Crompton & Knowles Corp., Charlotte, N.C.) such as INTRAWITE ® CF, etc.; a Leucophor (available from Sandoz Chemicals Corp., Charlotte, N.C.) such as Leucophor BS, Leucophor BSB, Leucophor EKB, Leucophor PAB, etc.; a Phorwite (available from Mobay Chemicals, Pittsburg, Pa.) such as Phorwite AR, Phorwite BBU, Phorwite BKL, Phorwite CL, Phorwite RKK, etc. and the like. Particularly preferred potentiating agents are Blancophor BBH, Phorwite AR and Calcofluor White M2R.

Photoproducts or other derivatives of Calcofluor White, for instance, may encompass the aldehyde, the cis-isomer or the reduced derivative thereof. As a representative compound of the stilbenes, Calcofluor White is usually in the trans-form (III) while the major initial photoproduct is the cis-form (IV). The cis-stilbene can be formed from Calcofluor White M2R by room light, sun light, GROW-LUX ® light or ultraviolet light from sun light. The conversion in dilute solution (0.02% w/w) is rapid and essentially complete in less than 6 hours of exposure to GROW-LUX ® or window light. The aldehyde (V) is prepared from Calcofluor White by permanganate catalyzed periodate oxidation at a pH of 8. The acid (VI) is formed by aerobic oxidation of the aldehyde (V). The reduced compound (VII) can be prepared by hydrogenation of Calcofluor White (III) by a 5% aqueous solution of Pd/C with 1N NH4OH. Evaporation of the aqueous solution and extraction of the black residue by warm methanol, filtration and evaporation of the extract gives the reduced compound (VII). For illustration, these stilbene compounds are shown below:

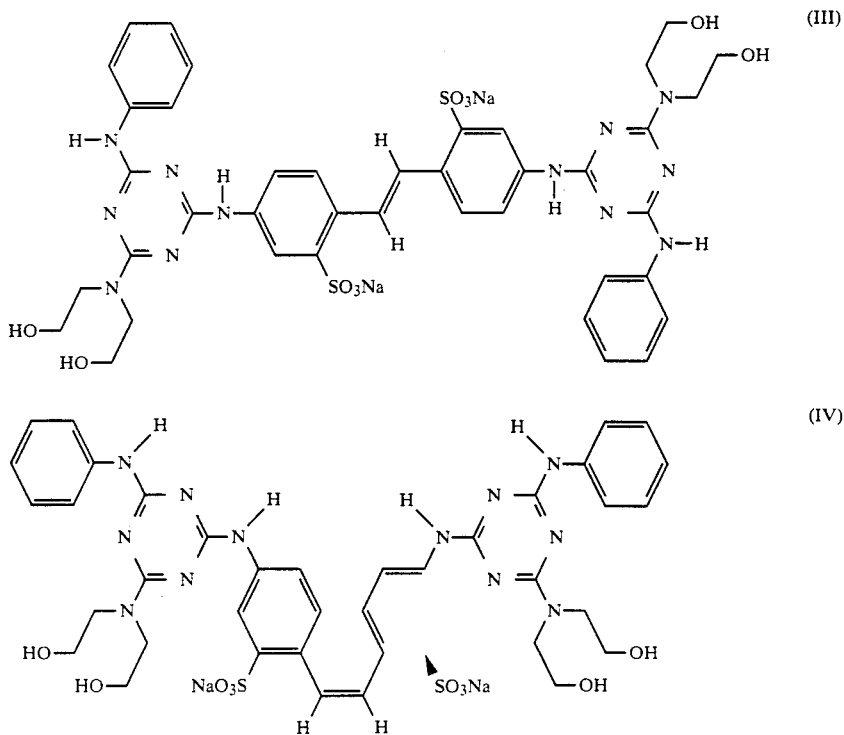

-continued

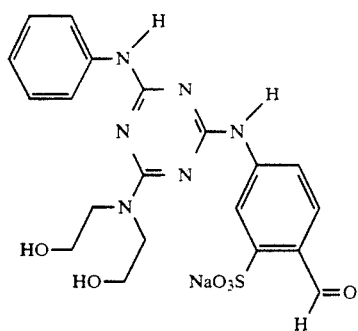
(V)

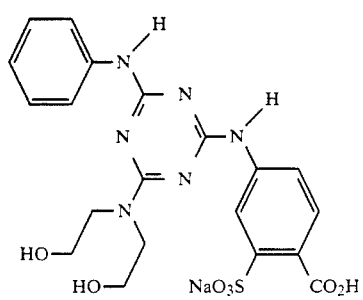
(VI)

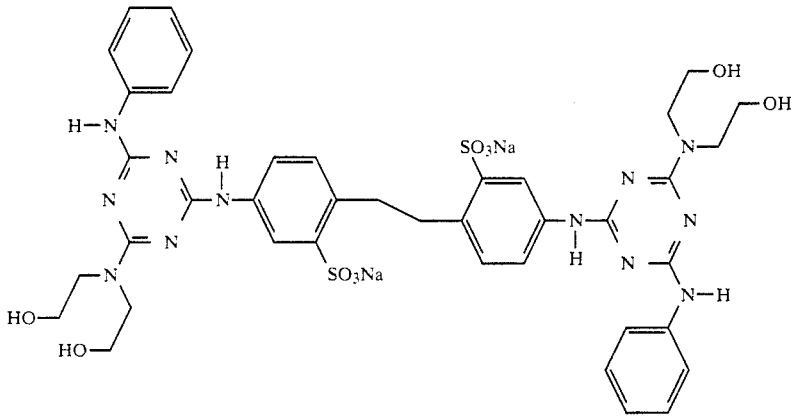
(VII)

The compositions of this invention containing the pesticide and the potentiating agent can be applied in either liquid or solid form. Solid form such as dusts or dust concentrates, or liquid form such as emulsifiable concentrates, flowable liquids, aqueous suspension concentrates or wettable powders can be dispersed in water or other inexpensive liquid for application as a finely divided spray. The combination compositions may be applied by conventional methods (e.g., aqueous foliar spray) to row, orchard or ornamental crops for control of phytophagous insects as well as domestic and health related pests. Alternatively, the stilbene compound can be employed as a spray adjuvant rather than one of the ingredients in the pesticide formulation. In this instance, the stilbene compound would be mixed with the diluent and the pesticide just prior to application. As a further alternative, the pesticide and the stilbene compound may be formulated in separate products and then applied simultaneously or sequentially in joint treatments of the desired areas. Also, the compositions may be prepared in various conventional bait formulations for application to the habitat or food supply of the pests or any area in which the pests may be found.

Surprisingly, by using the active ingredient in combination with the potentiating agent, a biological formulation is produced which is highly effective against phytophagous insects. Advantageously, there is a substantial decrease in the usual amount of pesticide needed to achieve control of the insects. The compositions are used to manage phytophagous insects by potentiation of the chemical insecticide induced by the stilbene compound. In particular, the compositions of this invention are very valuable for chemical insecticides like the pentadienone hydrazones which have low absorptive or penetrative properties through the insect's gut upon ingestion. Consequently, the compositions of the present invention provide an improved pest control with a concomitant increase in crop yield and lowered crop production costs owing to the reduced insecticide dose. The reduced insecticide dose further benefits the environment by decreased environmental contamination caused by chemicals.

Control of insects, particularly Lepidopterous, Orthopterous, Dipterous, Isopterous and Hymenopterous insects as well as Mollusca, Acarus and Nematoda (e.g., ants, flies, termites, cockroaches, snails, mites, parasitic worms, etc.) and protection of agronomic crops, trees, shrubs and ornamentals, from attack by the insects, acarina, mollusks and nematodes can be achieved by the application of an insecticidally, acaricidally, molluscicidally or nematocidally effective amount of the pesticide to the plants or to the habitat or food supply of the pests. The active ingredients are typically applied to the area to be treated in a wide range of useful concentrations. In practice, for example, generally about 0.1 kg/hectare to about 10.0 kg/hectare, and preferably about 0.1 kg/hectare to about 1.0 kg/hectare, of the pentadienone hydrazone is effective for insect control and/or for crop protection. For the cinnamamides, the effective amounts range typically from about 0.25 kg/hectare to about 8.0 kg/hectare, and preferably from about 0.25 kg/hectare to about 4.0 kg/hectare. The insecticidal amount of rotenone usually ranges from about 1.0 kg/hectare to about 100.0 kg/hectare, and desirably from about 1.0 kg/hectare to about 50.0 kg/hectare.

To potentiate the pesticidal activity, the stilbene compound is applied jointly, either simultaneously or sequentially, at the rate of about 0.01% w/v (weight of active ingredient to finished spray volume) to about 5.0% w/v, and desirably about 0.1% w/v to about 1.0% w/v. The aforenoted stilbene photoproducts (above compounds identified as formulas IV-VII) may typically be applied at the lower concentrations around 0.1% w/v. Nevertheless, amounts that are either above or below the specified ranges can also be used, though generally less favorably.

In combination with the stilbene compounds, the toxicity of the pentadienone hydrazones of this invention is substantially potentiated against insects of the orders Orthoptera and Diptera and especially active and very selective against Lepidopterous larvae such as southern armyworms (*Spodoptera eridania* (Cramer)), cabbage loopers (*Trichoplusia ni* (Hübner)), tobacco budworms (*Heliothis virescens* (Febricus)), gypsy moth (*Porthetria dispar* (L.)), and the like, at about 10 ppm to about 1000 ppm rates. Beneficially, the stilbene compound significantly potentiates the efficacy of the pesticidal agent. For example, leaves treated with the combinations of Calcofluor White M2R plus hydramethylnon surprisingly sustain much lower levels of *H. virescens* and *S. eridania* larval feeding (25% to 75% lower) than leaves treated with corresponding doses of hydramethylnon alone. Besides potentiation of the pesticide toxicity, the stilbene compound can protect the chemical pesticide from photodegradation. In the case of hydramethylnon which is unstable to light, the ability of the stilbene compound to increase the photostability of hydramethylnon provides a unique advantage.

Since the low toxicity to most beneficial insects does not appear to be altered, the combination is useful for pest management and integrated control programs. Additionally, the above-identified hydrazone compounds continue to exhibit relatively low mammalian toxicity and virtually no phytotoxicity to plants at rates of application up to 11.2 kg/hectare.

Advantageously, the pentadien-3-one hydrazone compounds of this invention act as stomach poisons and the combination composition are therefore effective against insects with chewing mouth parts as well as those with sponge and lapping mouth parts. They are especially effective for the control of ants, Family Formicidae, and may be used for the control of fire ants such as the southern fire ant (*Solenopsis xyloni* (xyloni)); leaf-cutting ants (*Acromyrmex versicolor* (Pergande)); Argentine ants (*Iridomyremex humilis* (Mayr)); black carpenter ants (*Camponotus pennsylvanica* (DeGeer)); cornfield ants (*Lasius alienus* (Foerster)); pavement ants (*Tetramorium caespitum*); larger yellow ants (*Acanthomyops interjectus* (Mayr)); thief ants (*Solenopsis molesta* (Say)); the red imported fire ant (*Solenopsis invicta* (Bruen)); and the black imported fire ant (*Solenopsis saevissima richteri*). These ants are serious economic pests generally found in the warmer climates such as the subtropical and tropical zones. They feed on seeds and tender stems of young plants and are responsible, annually, for substantial damage to agronomic crops. They have likewise been known to attack humans, nesting birds, livestock, poultry and household pets. As such, it is most desirable to control these economic pests.

Similar to the hydrazones, the cinnamamide compounds which are useful in the present invention act as stomach and contact poisons. These compounds in combination with the stilbene compounds are particularly effective for protecting crops, such as rice, grown in flooded paddies and irrigated crop plants, where the active compound is dispersed in the water of the flooded paddies or applied to the soil in the locus of the irrigated plots. About 10 ppm to about 10,000 ppm, and preferably about 100 ppm to about 5,000 ppm, of the active cinnamamide dispersed in the water is effective for protecting crops from attack by insects and acarina. When the active compound is applied to soil, about 0.25 kg/ha to about 8.0 kg/ha of active ingredient is sufficient to protect the crops against attack by insects and acarina.

The cinnamamides are especially effective for controlling Lepidopterous, Dipterous, Homopterous, Coleopterous, Hemipterous insects as well as acarina like the plant mites. For instance, the cinnamamide compounds are effective against such pests as tobacco budworm (*Heliothis virescens*), third-instar larvae, southern armyworm (*Spodoptera eridania*), adult common malarial mosquito (*Aropheles quadrimaculatus*), adult tarnished plant bug (*Lygris lineolaris*), adult western potato leafhopper (*Empoasca abrupta*) and adult male German cockroach (*Blattella germanica*), as well as others. Also, the cinnamamides are effective acaricides against P-resistant strain, adult two-spotted spider mite (*Tetranychus urticae*), etc.

Improved control of these pests can be achieved with treated baits that are distributed in the crop area, pasture, park or other location in which pest control is desired. Baits can be prepared, for example, by admixing the active ingredient and the stilbene compound with peanut butter, citrus pulp, apple pumice, wheatbran, corn meal-sugar, vegetable oils such as soybean oil or other feeding attractants and distributed as is; or these compositions with appropriate adjuvants can be coated onto carriers such as corn cob grits, clays, pumice, synthetic polymer compositions or the like and distributed in the area of the colony. Use of these baits has particular advantage, since such method of distribution poses little or no hazard to animals that may frequent the crop area.

A further understanding of the present invention can be obtained from the following examples. However, the examples are set forth only for the illustration of certain aspects of the invention and are not to be construed as limitations thereon. Unless otherwise expressed, all parts are by weight.

EXAMPLE 1

Evaluation of the Stilbene Compounds on Toxicity of Pentadienone Hydrazones to Tobacco Budworms Impact of the stilbene compounds on the toxicity of pentadienone hydrazones to tobacco budworms (TBW) is determined via a leaf-dip technique. Technical grade Calcofluor M2R (Sigma Chemical Co., St. Louis, MO) and hydramethylnon are used in this study. Equal-sized leaves are excised from three-week-old cotton plants which are grown in the greenhouse. Each leaf is immersed in an acetone+water (50+50 parts by volume) solution of a treatment for a period of about three seconds. To promote uniform distribution of active ingredients over leaf surfaces, an emulsifier (EMULPHOR® EL620, Rhone Poulenc, Princeton, N.J.) is added to all treatment solutions; EL620 comprises 0.1% by volume of each treatment solution. After immersion in the insecticide solutions, leaves are allowed to air-dry for about two hours. Plastic jelly trays are utilized as test arenas in this study. Each tray possesses 50 open-faced cells; dimensions of each cell are 4.0×3.0 ×1.5 cm (L×W×H). A 2.0×3.0 cm portion of a treated cotton leaf, a moistened (deionized water) cotton fiber dental wick and a third-instar TBW larvae are placed in each cell. Jelly tray cells are then covered with a clear plastic sheet, which in turn is sealed over the cells (to prevent larval escape) by using a hot iron. To monitor mortality of TBW larvae due to factors other than treatment intoxication, larvae are placed on leaves treated only with acetone+water+EL620 (i.e., diluent control) as well as on leaves treated only with acetone+water+EL620+M2R (i.e., synergist control).

All test arenas are held under constant fluorescent light (GRO-LUX® 40W, Sylvania) and a temperature of 27° C. throughout the post-infestation period. Larval mortality is measured 72 hours after infestation. Moribund larvae (i.e., larvae which are unable to right themselves within 20 seconds after being positioned ventral side up) are classified as dead. Based on counts of live and dead larvae, $LC_{50}$ values (in ppm) and respective 95% confidence intervals are determined for each treatment by using a computer log-probit analysis program (SAS Institute Inc., Cary, N.C. 1987).

Based on $LC_{50}$ values (and non-overlapping confidence intervals), a 1.0% w/v concentration of Calcofluor White M2R is found to potentiate the toxicity of hydramethylnon against third-instar *Heliothis virescens* by nearly two-fold. A 2.0% w/v concentration of Calcofluor White M2R is also found to potentiate the toxicity of hydramethylnon against *H. virescens* by about two-fold. Conversely, a 0.1% w/v concentration of M2R does not significantly enhance toxicity of hydramethylnon against *H. virescens*. Data obtained are reported in Table I below.

TABLE I

Impact of Calcofluor M2R on Toxicity of Hydramethylnon to Third-Instar *Heliothis virescens*

| Treatments | $N^{1,2}$ | $LC_{50}$ in ppm (95% CI) |
|---|---|---|
| Hydramethylnon | 191 | 108.6 (94.0–125.1) |
| Hydramethylnon + M2R (0.1% wt/vol) | 179 | 83.4 (68.5–102.7) |
| Hydramethylnon + M2R (1.0% wt/vol) | 206 | 54.6 (43.7–65.5) |

[1] N = number larvae tested, excluding controls (mean mortality in acetone + water control is 5%; mean mortality in 1.0% M2R control is 12%).
[2] Larvae used in this study are four to five days old and weigh around 20.9 mg (std. deviation = 4.2).

EXAMPLE 2

Evaluation of the Stilbene Compounds on Toxicity of Pentadienone Hydrazones to Southern Armyworms Impact of the stilbene compounds on toxicity of pentadienone hydrazones to southern armyworms (SAW) is determined via a leaf-dip technique. Calcofluor M2R and technical grade hydramethylnon are used in this study. Equal-sized leaves are excised from three-week-old "Sieva" lima bean plants which are grown in the greenhouse. Each leaf is immersed in an acetone+water (50:50 dilution)+EL620 solution of a treatment for a period of about three seconds. After immersion in the insecticide solution, leaves are allowed to dry for about two hours. Leaves are then individually placed in plastic Petri dish bottoms (100 mm diameter). Each dish contains three sheets of water-moistened filter paper (Whatman #1) to keep the leaf turgid throughout the duration of the assay. Each leaf is infested with 10 third-instar SAW larvae, and plastic covers are subsequently placed over Petri dish bottoms. To monitor mortality of larvae due to factors other than intoxication from insecticides, larvae are placed on leaves treated only with acetone+water+EL620 (i.e., diluent control) as well as on leaves treated only with acetone+water+EL620+M2R (i.e., synergist control).

All test arenas are held under constant fluorescent light (GRO-LUX®) and a temperature of 27° C throughout the post-infestation period. At three days post-infestation, fresh untreated lima bean leaves are placed in arenas which are void of foliage as a result of consumption by SAW. Larval mortality is measured five days after initial infestation. Moribund larvae (i.e., larvae which are unable to right themselves within 20 seconds after being positioned on their dorsal side) are classified as dead. Based on counts of live and dead larvae, $LC_{50}$ values (in ppm) and respective 95% confidence intervals are determined for each treatment by using a computer log-probit analysis program (SAS Institute Inc., Cary, N.C. 1987).

Although $LC_{50}$ confidence intervals overlap, there is a strong trend indicating that a 1.0% w/v concentration of M2R enhances toxicity of hydramethylnon by about two-fold against third-instar *Spodoptera eridania*. Data obtained are reported in Table II below.

TABLE II

Impact of Calcofluor M2R on Toxicity of Hydramethylnon to Third-Instar *Spodoptera eridania*

| Treatments | $N^1$ | $LC_{50}$ ppm (955 CI) |
|---|---|---|
| Hydramethylnon | 834 | 29.8 (19.8–90.7) |
| Hydramethylnon + M2R (1.0% wt/vol) | 715 | 14.1 (6.2–54.3) |

[1] N = number of larvae tested, excluding controls (mean mortality in acetone + water and 1.0% M2R controls are less than 5%).

EXAMPLE 3

Evaluation of an Aldehyde Photoproduct of a Stilbene Compound on Toxicity of Pentadienone Hydrazones to Tobacco Budworm To prepare the aldehyde photoproduct, 4.0 g of Calcofluor White M2R and 1.0 g of $Na_2CO_3$ are added to 100 mL of water, stirred and cooled in ice water. The pH of the mixture is about 8.5. Then, a catalytic amount of $KMnO_4$ (0.075 g) and 1.15 g of $NaIO_4$ are added. The ice bath is removed and the reaction is allowed to proceed at ambient temperature. After 2 hours, an additional 0.083 g of $NaIO_4$ and 0.53 g of $NaIO_4$ are added, and allowed to stir overnight at room temperature. Then, 0.20 g of $NaIO_4$ and 1.15 g of $NaIO_4$ are added. After 2 hours, the HPLC shows that the reaction has proceeded to completion. The salts are removed from the aldehyde by adding 200 mL of methanol and stirred for an hour. The solution is filtered and concentrated on a rotary evaporator under reduced pressure. To the residue is added 200 mL of methanol, stirred warm, allowed to stand overnight at room temperature and then again filtered. The methanol is removed on a rotary evaporator under reduced pressure. The solid residue is dried for one hour at 65° C at 0.2 mm Hg to give 4.28 g of the aldehyde as a yellow powder. Structure is confirmed by $^1H$ NMR.

Methods which are used in this study follow those described in Example 1. Enhancement of hydramethylnon by the aldehyde photoproduct of Calcofluor White M2R is seen as erratic when comparing hydramethylnon at 40 ppm vs. 80 ppm. The results show a slight potentiation of hydramethylnon against *H. virescens*. The M2R aldehyde is less effective than the "parent" M2R as a potentiator of hydramethylnon (i.e., when compared at the hydramethylnon concentration of 40 ppm). The results are shown in Table III below.

TABLE III

Impact of Calcofluor M2R and an Aldehyde Photoproduct of Calcofluor M2R on Toxicity of Hydramethylnon to Third-Instar *Heliothis virescens*

| Treatments | % larval mortality | | |
|---|---|---|---|
| | Rep I[1] | Rep II | Mean |
| Hydramethylnon (80 ppm) | 79 | 40 | 60 |
| Hydramethylnon (80 ppm) + 1.0% M2R | 93 | 80 | 87 |
| Hydramethylnon (80 ppm) + 1.0% M2R Aldehyde | 93 | 67 | 80 |
| Hydramethylnon (40 ppm) | 27 | 40 | 34 |
| Hydramethylnon (40 ppm) + 1.0% M2R | 73 | 47 | 60 |
| Hydramethylnon (40 ppm) + 1.0% M2R Aldehyde | 64 | 20 | 42 |
| 1.0% M2R control | 13 | 7 | 10 |
| 1.0% M2R Aldehyde control | 13 | 13 | 13 |
| Untreated control | 7 | 13 | 10 |

[1]Each treatment replication consists of 13-15 larvae.

EXAMPLE 4

Evaluation of the Stilbene Compounds on Toxicity of Pentadienone Hydrazones to Third-Instar *Heliothis virescens*

To confirm the existence of potentiation of the pentadienone hydrazones by stilbene compounds, an additional series of treatment replications is conducted by utilizing larvae form two other laboratory colonies of *H. virescens* obtained from Ecogen Inc. (Langhorn, Pa.) and USDA/ARS (Stoneville, Miss.). With the exception of the test arenas, materials and methods utilized in this assay are identical to those used in Example 1. Bioassay trays manufactured by C-D International, Inc. (Pitman, N.J.) are used in this assay. Each tray contains 32 open-faced cells; dimensions of each cell are $4.0 \times 4.0 \times 2.5$ cm (L×W×H). After larval infestation, each cell is covered with a vented clear plastic sheet (C-D International, Inc.). Based on $LC_{50}$ values, 1.0% w/v and 2.0% w/v concentrations of Calcofluor White M2R each potentiate toxicity of hydramethylnon against third-instar *H. virescens* by around two-fold. The results are shown in Table IV below.

TABLE IV

Impact of Calcofluor White M2R on Toxicity of Hydramethylnon to Third-Instar *Heliothis virescens*

| Treatments | $N^{1,2}$ | $LC_{50}$ in ppm | 95% CI | Std. error |
|---|---|---|---|---|
| Hydramethylnon | 319 | 159.2 | (—)[3] | 24.8 |
| Hydramethylnon + M2R (2.0% w/v) | 398 | 74.5 | (67.1-82.3) | 3.8 |
| Hydramethylnon + M2R (1.0% w/v) | 398 | 67.4 | (60.1-74.9) | 3.7 |

[1]N = number larvae tested, excluding controls (mean mortality in acetone + water control is 2%; mean mortality in 2.0% M2R control is 4.0%).
[2]Larvae used in this study ar four to five days old.
[3]Unable to generate confidence interval.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

We claim:

1. A composition for enhanced insecticidal activity, comprising a potentiating effective amount of Calcofluor White M2R and an insecticidally effective amount of a pentadienone hydrazone compound having the structure of formula I:

$$R_1 \underset{R_3}{\underset{|}{\bigcirc}} -HC=CH-\underset{\underset{R_6}{|}}{\overset{\overset{N-R_4}{\underset{\|}{\overset{NH-C}{\diagdown}}}}{C}}-CH=CH- \underset{R_3}{\underset{|}{\bigcirc}} R_2 \quad (I)$$

wherein $R_1$ and $R_2$ each represent hydrogen, halogen, $CF_3$, $C_1$-$C_4$ alkyl, $C_1$-$C_4$ alkoxy or $C_1$-$C_4$ alkylthio; $R_3$ is hydrogen or methyl, provided that when $R_3$ is methyl, $R_1$ and $R_2$ are also methyl; $R_4$ and $R_5$ represent hydrogen or $C_1$-$C_4$ alkyl, and when taken together, an alkylene group of 2 to 6 carbon atoms, a methyl substituted or a phenyl substituted alkylene group of 2 to 4 carbon atoms, a dimethyl substituted alkylene group of 2 to 4 carbon atoms or 1,2-cyclohexylene; and $R_6$ is hydrogen or $C_1$-$C_4$ alkyl; or a salt thereof.

2. The composition according to claim 1, wherein the compound is 1,5-bis($\alpha,\alpha,\alpha$-trifluoro-p-tolyl)-1,4-pentadien-3-one (1,4,5,6-tetrahydro-5,5-dimethyl-2-pyrimidinyl) hydrazone.

3. A method for enhancing insecticidal toxicity against an insect, which comprises contacting the insect, with, or applying to its habitat or food supply, an insecticidally effective amount of the composition of claim 4.

4. The method according to claim 3, which comprises contacting the insect with or applying to its habitat or food supply the compound 1,5-bis(α,α,α-trifluoro-p-tolyl)-1,4-pentadien-3-one (1,4,5,6-tetrahydro-5,5-dimethyl-2-pyrimidinyl) hydrazone.

5. An improved method for protecting agronomic crops, trees, shrubs and ornamentals from attack by an inset which comprises applying to a plant an insecticidally effective amount of the composition of claim 4.

* * * * *

UNITED STATES PATENT AND TRADEMARK OFFICE
CERTIFICATE OF CORRECTION

PATENT NO. : 5,246,936
DATED : September 21, 1993
INVENTOR(S) : Michael F. Treacy; Bruce C. Black; Stephen F. Donovan It is certified that error appears in the above-identified patent and that said Letters Patent is hereby corrected as shown below:

At the bottom of column 6, compound IV, that portion of the structure reading

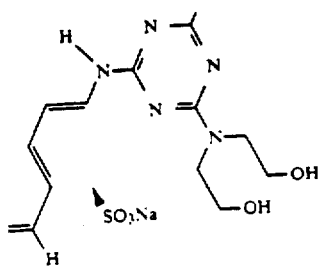   should read   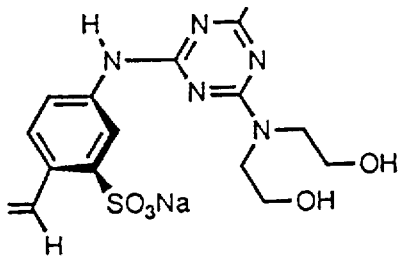

```
Col. 15, Claim 3, line 2, "claim 4" should read --claim 1--.
Col. 16, Claim 5, line 5, "inset" should read --insect--; and,
    line 6, "claim 4" should read --claim 1--.
```

Signed and Sealed this

Eighteenth Day of October, 1994

Attest:

BRUCE LEHMAN

Attesting Officer

Commissioner of Patents and Trademarks